United States Patent [19]

Martin

[11] 4,227,917
[45] Oct. 14, 1980

[54] PHENYLGLYOXYLONITRILE-2-OXIME-CYANOMETHYL ETHER AS A CROP SAFENER

[75] Inventor: Henry Martin, Allschwil, Switzerland

[73] Assignee: Ciba-Geigy Corporation, Ardsley, N.Y.

[21] Appl. No.: 23,805

[22] Filed: Mar. 26, 1979

Related U.S. Application Data

[63] Division of Ser. No. 772,700, Feb. 28, 1977, Pat. No. 4,152,137, which is a continuation-in-part of Ser. No. 717,792, Aug. 25, 1976, Pat. No. 4,070,389.

[51] Int. Cl.² .......................... A01N 9/12; A01N 9/20
[52] U.S. Cl. .......................................... 71/100; 71/88; 71/103; 71/105; 71/118
[58] Field of Search .................... 71/100, 88, 103, 105

[56] References Cited

U.S. PATENT DOCUMENTS

| 3,515,536 | 6/1970 | Hill et al. | 71/77 |
| 3,578,434 | 5/1971 | Noveroske et al. | 71/77 |
| 3,799,757 | 3/1974 | Dixon et al. | 71/105 |
| 3,928,436 | 12/1975 | Tilles et al. | 71/103 |
| 4,140,516 | 2/1979 | Scher | 71/88 |
| 4,152,137 | 5/1979 | Martin | 71/105 |

FOREIGN PATENT DOCUMENTS 487331  3/1973  Japan .......................................... 71/77

Primary Examiner—Glennon W. Hollrah
Attorney, Agent, or Firm—Frederick H. Rabin

[57] ABSTRACT

The new compound phenylglyoxylonitrile-2-oxime-cyanomethylether of the formula

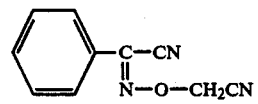

and compositions containing it, are used as a safener (antidote) for selectively combatting weeds in culture crops, especially sorghum and rice, in order to protect these cultivated plants from being injured by strong herbicides such as chloroacetanilides and thiolcarbamates. The safener is preferably applied to the crop seeds prior to planting.

9 Claims, No Drawings

PHENYLGLYOXYLONITRILE-2-OXIME-CYANOMETHYL ETHER AS A CROP SAFENER

CROSS REFERENCE TO RELATED APPLICATION

This is a division of application Ser. No. 772,700 filed on Feb. 28, 1977 now U.S. Pat. No. 4,152,137, which is a continuation-in-part of application Ser. No. 717,792, filed on Aug. 25, 1976, now U.S. Pat. No. 4,070,389.

BACKGROUND OF THE INVENTION

The present invention relates to a novel oxime ether, to processes for producing it, to its use as an antidote (safener) for herbicides which damage certain cultivated plants, so that such herbicides can be employed as selective herbicides, without loss of their herbicidal action against weeds, in crops of these cultivated plant. The invention relates also to compositions containing said oxime ether, optionally together with a herbicide.

It is known that herbicides of the most varied classes of substances, such as triazines, urea derivatives, carbamates, thiolcarbamates, halogenoacetanilides, halogenophenoxyacetic acids, etc., have in the case of cultivated plants an action that is not selective or insufficiently selective, with the result that these herbicides attack not only the weeds to be combatted but to a lesser or greater extent also the cultivated plants.

Various substances have already been suggested for overcoming this problem, which substances are able to specifically antagonise the harmful action of the herbicide on the cultivated plant, i.e. to protect the cultivated plant without noticeably affecting the herbicidal action on the weeds to be combatted. Depending on its properties, the antidote can be used before emergence (pre-emergence) or after emergence (post-emergence) of the plants. For example, it can be used for pretreatment of the seed of the cultivated plant (seed dressing); it can be applied into the seed furrows before sowing; it can be used for the pretreatment of cuttings; or, finally, it can be applied as a tank mixture. Furthermore, it can be employed together with the herbicide, and can be applied either by one or by several of the foregoing methods. The treatment with the antidote can be carried out before or after the herbicidal treatment, or the two treatments can be performed simultaneously. The pre-emergence treatment includes both the treatment of the cultivated area before sowing (ppi=pre plant incorporation) and the treatment of the sown cultivated area before emergence of the plants.

The suggested antidotes frequently have an action that is very specific to the species with regard to the cultivated plants (e.g. maize, cereals such as wheat, etc., rice, sorghum, soybean, cotton, sugar cane, etc.) and with regard to the type of active substance of the herbicide (triazines, carbamates, etc.) and often also with regard to the type of application (seed dressing, pre-emergence tank application, etc.); i.e. a specific antidote is frequently suitable only for a specific cultivated plant and for certain herbicidal classes of active substance.

Thus, British Pat. No. 1,277,557 describes the protective treatment of seed and of shoots of wheat and sorghum with certain oxamic acid esters and amides in order to avoid the harm caused by alachlor (N-methoxymethyl-2,6-diethyl-chloroacetanilide). According to other references (German Offenlegunesschriften Nos. 1,952,910, 2,245,471 and French Pat. No. 2,021,611), antidotes are suggested for the treatment of cereals, maize seed and rice seed for protection against the attack from herbicidal thiolcarmabamates. In German Pat. No. 1,576,676 and U.S. Pat. No. 3,131,509, there are suggested hydroxyamino-acetanilides and hydantoins for the protection of the seed of cereals against carbamates such as isopropyl, N-phenylcarbamate, isopropyl m-chlorocarbanilate, etc. In U.S. Pat. Nos. 3,996,043 and 3,998,621, there are described certain antidotes for use with triazine herbicides which permit the herbicides to be used in cotton cultures.

The direct treatment of certain useful plants before or after emergence of the plants on a cultivated area with antidotes as antagonists of specific classes of herbicides is described in German Offenlegungsschriften Nos. 2,141,586 and 2,218,097 and in U.S. Pat. No. 3,867,444.

Whilst maize plants can be excellently protected from damage that can result from strongly herbicidally effective chloroacetanilides, such as have been described in German Offenlegungsschriften Nos. 2,212,268, 2,305,495 and 2,328,340, by an N-substituted dichloroacetamide being applied as antidote to the soil (German Offenlegungsschrift No. 2,402,983), corresponding tests in other crops, such as cultivated millet and rice, have been unsuccessful.

It is therefore a principal object of this invention to provide an antidote (safener) compound which will permit the use of chloroacetanilide herbicides, and other effective weed killers in cultivated crops, particularly sorghum and rice.

SUMMARY OF THE INVENTION

It has now been found that the novel oxime ether of formula I

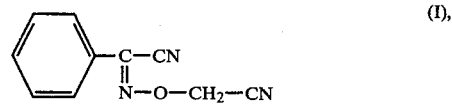

which can be designated as [O-(cyanomethyl)-oximino]-benzylcyanide as [O-(cyanomethyl)-oximino]-αcyanotoluene, or as phenylglyoxylonitrile-2-oxime-xyanomethyl ether, is excellently suitable for the protection of cultivated plants, such as maize, varieties of cereals (wheat, rye, barley, oats, etc.), cotton, sugar beet, sugar cane, soybean, etc., especially however cultivated millet of the sorghum genus, such as *S. vulgare* and *S. hybridum*, as well as rice, from the attack of herbicides of the most varied classes of substances, such as triazines, phenylureas, carbamates, benzoic acid derivatives, halogenophenoxyacetic acids, etc., particularly however from the attack of herbicidal halogenoacetanilides and thiolcarbamates.

DETAILED DISCLOSURE

The free phenylglyoxylonitrile-2-oxime from which the above ether derives and some ring-substituted derivatives of the free oxime are described in U.S. Pat. No. 3,799,757 as growth inhibitors for regulating the growth in height of maize, cereals and soybeans, i.e. for a completely different field of application.

The novel oxime ether of formula I is produced according to the invention by reaction of a salt, especially an alkali metal salt, of phenylglyoxynitrile-2-oxime of formula II

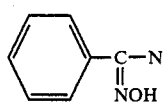

(II)

with a cyanomethyl halide (halogenoacetonitrile) of the formula Hal—$CH_2$—CN.

The starting oxime of formula II is known and can be produced, for example, according to *Organic Reactions* 7, pp. 343 and 373 (1953). It is known that oximes can exist in two stereoisomeric forms, the syn- and anti-form. Also the oxime ether of formula I according to the invention can exist in both forms and as a mixture thereof. Accordingly, within the scope of the present description are meant both stereoisomeric forms either separately or as a mixture in any reciprocal mixture ratio.

The following Example illustrates the production of the novel oxime ether of formula I.

EXAMPLE I

Preparation of Antidote Compound 33.8 g of phenylglyoxylonitrile-2-oxime (sodium salt) is suspended in 200 ml of acetonitrile in a 350 ml sulphonating flask. An addition is then made dropwise of 15.1 g of chloroacetonitrile in 20 ml of acetonitrile, whereupon a very slight increase in temperature can be observed. The suspension is subsequently refluxed with stirring for 3 hours, during the process of which the reaction mixture assumes a light-green colour. After cooling to room temperature, the formed sodium chloride is filtered off with suction, and the filtrate is concentrated in a rotary evaporator to obtain as residue 31 g of crude product. This is dissolved in 200 ml of acetonitrile; the solution is stirred with charcoal and filtered until clear. Concentration of the filtrate in the rotary evaporator yields 25.4 g of oxime ether (68.6% of theory), m.p. 53°–54° C.

Recrystallised from isopropanol, the pure phenyl-glyoxylonitrile-2-oxime-cyanomethyl ether melts at 56°–57° C. (syn-form). The other stereoisomeric form (anti) of this ether melts at 58°–59° C. and has a boiling point of 136° C./0.05 torr. Chloroacetanilides usable as highly effective active substances which on their own damage cultivated plants, such as cereals, rice, sorghum hyb. and cultivated millet varieties, but which when used together with the oxime ether according to the invention no longer appreciable attack these cultivated plants whilst retaining the herbicidal effectiveness against weeds, have become known, for example, U.S. Pat. No. 3,547,620, U.S. Pat. No. 3,403,994, U.S. Pat. No. 3,442,945, U.S. Pat. No. 3,637,847, U.S. Pat. No. 3,598,859, U.S. Pat. No. 3,819,661, U.S. Pat. No. 3,946,045, U.S. Pat. No. 3,983,174, also from German Offenlegungsschrift Nos. 2,212,268, 2,305,495, 2,328,340, 2,402,983, 2,405,183 and 2,405,479.

The antidote according to the invention is preferably used together with herbicidal chloroacetanilides which correspond to the formula III

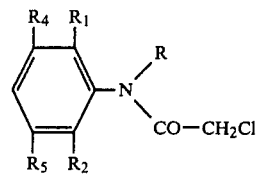

(III)

wherein $R_1$ is a lower alkyl, alkoxy, alkoxyalkyl or trifluoromethyl group or a halogen atom, and $R_2$, $R_4$ and $R_5$ independently of one another are hydrogen, a lower alkyl, alkoxy, alkoxyalkyl or trifluoromethyl group or a halogen atom, and R is an alkyl group having 1 to 4 carbon atoms which may be substituted by carboxy, carboxylic acid ester, carboxylic acid amide, carboxylic acid (mono- or di-lower aliphatic) amide or a cyano group; or wherein R is a propinyl, a butinyl, an acetalized carbonylalkyl, a 1,3-dioxolan-2-yl-alkyl, a 1,3-dioxolan-5-yl-alkyl, a 1,3-dioxan-2-yl-alkyl, a furanylmethyl, a tetrahydrofuranylmethyl group or an alkoxyalkyl group of the form —A—O—$R_3$, in which A is an alkylene group having 1 to 4 carbon atoms of which 1 or 2 are in the direct chain, and $R_3$ is a lower alkyl or alkenyl group or a cycloalkyl or cycloalkylmethyl group having 3 to 6 ring carbon atoms.

As used herein, the term "lower" as applied to alkyl groups and other hydrocarbon groups refers to groups having up to four carbon atoms. These include, in the case of lower alkyl, methyl, ethyl, n-propyl, isopropyl, n-butyl, isobutyl, sec. butyl and tert. butyl. By "halogen" is meant fluorine, chlorine, bromine and iodine, particularly fluorine and chlorine.

One of the groups of herbicidal chloroacetanilides preferably used are those where in the above formula III $R_1$ is hydrogen or alkyl having 1 to 4 carbon atoms, $R_2$ is alkyl having 1 to 4 carbon atoms, R is alkyl having 1 to 4 carbon atoms which is substituted by a carboxylic acid ester group, or an alkoxyalkyl group of the formula —A—O—$R_3$, wherein A is an alkylene group having 2 or 3 carbon atoms of which 1 or 2 are in the direct chain, $R_3$ is alkyl having 1 to 4 carbon atoms or alkenyl having 2 to 4 carbon atoms, and $R_4$ and $R_5$ are hydrogen.

Some herbicidal chloroacetanilides which can be used are listed below:

N-ethoxymethyl-2-methyl-6-ethyl-chloroacetanilide,
N-methoxymethyl-2,6-diethyl-chloroacetanilide,
N-(2'-methoxyethyl)-2,6-dimethyl-chloroacetanilide,
N-(2'-allyloxyethyl)-2,6-dimethyl-chloroacetanilide,
N-(2'-n-propoxyethyl)-2,6-dimethyl-chloroacetanilide,
N-(2'-isopropoxyethyl)-2,6-dimethyl-chloroacetanilide,
N-(2'-methoxyethyl)-2-methyl-6-ethyl-chloroacetanilide,
N-(2'-methoxyethyl)-2,6-diethyl-chloroacetanilide,
N-(2'-ethoxyethyl)-2-methyl-6-ethyl-chloroacetanilide,
N-(1'-ethoxycarbonyl-ethyl)-2,6-dimethyl-chloroacetanilide,
N-[3'-methoxyprop-(2')-yl]-2-methyl-chloroacetanilide,
N-[3'-methoxyprop-(2')-yl]-2,6-dimethyl-chloroacetanilide,
N-[3'-methoxyprop-(2')-yl]-2-methyl-6-ethyl-chloroacetanilide, N-[3'-methoxyprop-(2')-yl]-2,6-diethyl-chloroacetanilide,
N-[3'-methoxyprop-(2')-yl]-2-ethyl-chloroacetanilide,
N-(2'-ethoxyethyl)-2,6-diethyl-chloroacetanilide,
N-(2'-n-propoxyethyl)-2-methyl-6-ethyl-chloroacetanilide,
N-(2'-n-propoxyethyl)-2,6-diethyl-chloroacetanilide,
N-(2'-isopropoxyethyl)-2-methyl-6-ethyl-chloroacetanilide,
N-chloroacetyl-2,6-dimethylanilino-acetic acid ethyl ester,
N-chloroacetyl-2,6-diethylanilino-acetic acid ethyl ester,
N-chloroacetyl-2,6-dimethylanilino-acetic acid methyl ester,
N-chloroacetyl-2-methyl-6-ethylanilino-acetic acid isopropyl ester,
β-(N-chloroacetyl-2,6-dimethylanilino)-propionic acid methyl ester,
α-(N-chloroacetyl-2-methyl-6-ethylanilino)-propionic acid ethyl ester,
2-[N-(α-chloroacetyl)-2,6-dimethylanilino]acetaldehyde-diethylacetale,
N-[3'-methoxyprop-(2')-yl]-2,3-dimethyl-chloroacetanilide,
N-(2'-ethoxyethyl)-2-methyl-chloroacetanilide,
N-(2'-methoxyethyl)-2-methyl-chloroacetanilide,
N-[2'-methoxyprop-(1')-yl]-2,6-dimethyl-chloroacetanilide,
N-[2'-methoxyprop-(1')-yl]-2-methyl-6-ethyl-chloroacetanilide,
N-[3'-ethoxyprop-(2')-yl]-2-methyl-6-ethyl-chloroacetanilide,
N-(2'-ethoxyethyl)-2-fluoro-chloroacetanilide,
N-[3'-ethoxyprop-(2')-yl]-2-fluoro-chloroacetanilide,
N-[1'-methoxybut-(2')-yl]-2,6-dimethyl-chloroacetanilide,
N-(2'-methoxyethyl)-2-methyl-6-methoxy-chloroacetanilide,
N-(n-butoxymethyl)-2-tert.butyl-chloroacetanilide,
N-[3'-ethoxyprop-(2')-yl]-2,6-dimethyl-chloroacetanilide,
N-(2'-methoxyethyl)-2-chloro-6-methyl-chloroacetanilide,
N-(2'-ethoxyethyl)-2-chloro-6-methyl-chloroacetanilide,
N-(2'-ethoxyethyl)-2,3,6-trimethyl-chloroacetanilide,
N-(2'-methoxyethyl)-2,3,6-trimethyl-chloroacetanilide,
N-(2'-isopropoxyethyl)-2,3,6-trimethyl-chloroacetanilide,
N-cyanomethyl-2,6-dimethyl-chloroacetanilide,
N-(but-1-yn-3-yl)-chloroacetanilide,
N-propynyl-2-methyl-6-ethyl-chloroacetanilide,
N-(1,3-dioxolan-2-ylmethyl)-2,6-dimethyl-chloroacetanilide,
N-(1,3-dioxolan-2-ylmethyl)-2-ethyl-6-methyl-chloroacetanilide,
N-(1,3-dioxan-2-ylmethyl)-2-methyl-6-ethyl-chloroacetanilide,
N-(2'-furanyl-methyl)-2,6-dimethyl-chloroacetanilide,
N-(2'-furanyl-methyl)-2-chloro-6-methyl-chloroacetanilide,
N-(2'-tetrahydrofuranyl-methyl)-2,6-dimethyl-chloroacetanilide,
N-(N'-propargylcarbamylmethyl)-2,6-dimethyl-chloroacetanilide,
N-(N',N'-dimethylcarbamylmethyl)-2,6-dimethyl-chloroacetanilide,
N-(n-butoxymethyl)-2,6-diethyl-chloroacetanilide,
N-(2'-n-butoxyethyl)-2,6-diethyl-chloroacetanilide,
N-[3'-methoxybut-(2')-yl]-2,6-dimethylchloroacetanilide, 2-chloro-N-isopropylacetanilide.

Many of the herbicidal chloroacetanilides mentioned above and other herbicidal chloroacetanilides of this type and the production thereof have been described in the aforementioned U.S. patents and German Offenlegungsschriften.

The antidote of this invention may also be used with herbicidal compositions comprising the above described chloroacetanilide and other herbicidal compounds, e.g. triazine herbicides described in, e.g., U.S. Pat. Nos. 2,891,855 and 2,909,420.

Suitable thiolcarbamates which can be used as herbicides, especially in the case of pretreatment of the seed with the novel oxime ether, are those of the general type:

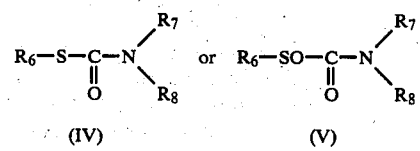

wherein
$R_6$ is a lower alkyl, alkenyl, chloroallyl, dichloroallyl, trichloroallyl or p-chlorobenzyl group, and
$R_7$ is a lower alkyl group having at least 2 carbon atoms,
$R_8$ is a lower alkyl group having at least 2 carbon atoms or a cyclohexyl group or wherein
$R_7$ and $R_8$ together with the nitrogen atom form the hexahydro-1H-azepin ring or the decahydroquinoline or 2-methyl-decahydroquinoline ring.

The following may for example be mentioned:
S-ethyl-N,N-dipropylthiocarbamate,
S-ethyl-N,N-diisobutylthiocarbamate,
S-2,3-dichloroallyl-N,N-diisopropylthiolcarbamate,
S-propyl-N-butyl-N-ethylthiolcarbamate,
S-2,3,3-trichloroallyl-N,N-diisopropylthiolcarbamate,
S-propyl-N,N-dipropylthiolcarbamate,
S-ethyl-N-ethyl-N-cyclohexylthiolcarbamate,
S-ethyl-N-hexahydro-1H-azepin-1-carbothioate,
S-isopropyl-N,N-hexamethylen-thiolcarbamate,
S-(p-chlorobenzyl)-N,N-diethylthiolcarbamate,
N-ethylthiocarbonyl-cis-decahydroquinoline,
N-propylthiocarbonyl-decahydroquinaldine,
S-ethyl-N,N-bis(n-butyl)-thiolcarbamate,
S-tert.butyl-N,N-bis(n-propyl)-thiolcarbamate.

Further examples of utilisable herbicidal thiolcarbamates are disclosed by the U.S. Pat. Nos. 2,913,327, 3,037,853, 3,175,897, 3,185,720, 3,198,786 and 3,582,314 pertinent portions of which are hereby incorporated by reference.

The applied amount of the antidote varies between about 0.01 and about 15 parts by weight per part by weight of halogenoacetanilide or thiolcarbamate. The most suitable ratio with regard to the optimum action in the case of the specific cultivated plant is determined from case to case, i.e. depending on the employed chloroacetanilide, thiolcarbamate, or other herbicidal compound.

As mentioned above, various methods and techniques can be employed for the use of the novel antidote compound of formula I together with herbicidal active substances or mixtures of active substances of the chloroacetanilide class and/or of the thiolcarbamate class.

1. Seed dressing (a) Dressing of the seed with an antidote formulated as a wettable powder by shaking of the constituents in a vessel until there exists a uniform distribution over the surface of the seeds (dry dressing). The amount of antidote used for this purpose is about 5 to 500 g (40 g to 2 kg of wettable powder) per 100 kg of seed.

(b) Dressing of the seed with an emulsion concentrate of the antidote by the method and with the amounts given under (a) (wet dressing).

(c) Dressing by immersion of the seed in a liquor containing 50–3200 ppm of antidote for 1–20 hours and subsequent drying of the seed (immersion dressing).

Seed dressing is the preferred mode of use of the antidote compound. The preferred amount of antidote ranges from about 50 to about 400 grams per 100 kg of seed. Particularly preferred amounts are from 100 to 250 grams per 100 kg of seed, notably from about 150 to about 200 grams per 100 kg of seed.

2. Application as tank mixture

A liquid preparation of a mixture of antidote and herbicide (quantitative ratio between 10:1 and 1:10) is used, with the applied amount of herbicide being 0.1 to 10 kg per hectare. This tank mixture is preferably applied before emergance (either before or after sowing), or it is worked into the unsown soil to a depth of 5–10 cm.

3. Application into the seed furrow

The antidote is introduced, as an emulsion concentrate, wettable powder or granulate, into the open sown seed furrows and, after the covering of the seed furrow in the normal manner, the herbicide is applied either before or after emergence of the plants.

The antidote can therefore be applied before, together with, or after the herbicide, and its application to the seeds or to the field before emergence can be effected either before or after sowing; or in certain cases it can be effected also after germination of the seed (post-emergence).

If the antidote is applied simultaneously with the herbicide, this is accomplished by the use of a preparation according to the invention, which preparation contains the oxime ether of formula I and at least one herbicide from the chloroacetanilide and/or thiolcarbamate class, together with additives such as carriers and/or distribution agents.

The method according to the invention for the selective control of weeds in cultivated crops, especially of the sorghum and rice genera, is such that the seeds of the cultivated plants or the cultivated areas intended for sowing or already sown, or on which the sown plants have already emerged, are treated, simultaneously, or successively in any desired sequence and at a suitable interval of time, on the one hand with phenylglyoxylonitrile-2-oxime-cyanomethyl ether of formula I as the antidote protecting the cultivated plants or the seed thereof, and on the other hand with at least one herbicidal active substance, preferably of the chloroacetanilide class and/or of the thiolcarbamate class.

The compositions used, which contain herbicide and antidote separately or together, can be in any suitable conventional form. They can be produced in a manner known per se by the intimate mixing and grinding of the active substance(s) (including antidote) with suitable carriers and/or distributing agents, optionally with the addition of dispersing agents or solvents.

The usual forms of such compositions are either solid, such as dusts, scattering agents and granulates, or liquid, such as solutions and aqueous dispersions; or they are water-dispersible concentrates of active substance, such as wettable powders, emulsion concentrates or pastes.

In addition to the "safener" action of the antidote of formula I according to the invention, there is observed a certain antagonising counteraction on the growth-inhibiting effect of some growth regulators on grasses in the case of overdosage of the growth ingibitor. Furthermore, the compound of formula I, used on its own, exhibits a germination-stimulating action on certain seed varieties, such as those of sorghum, rice, etc.

EXAMPLE II

Tests with Metolachlor

The following tests were carried out to determine the selective herbicidal action of a highly effective first-class herbicidal compound of the chloroacetanilide class, on its own or together with the antidote of formula I according to the invention. The compound is metolachlor, N-[3'-methoxyprop-(2')-yl]-2-methyl-6-ethyl-chloroacetanilide disclosed in U.S. Pat. No. 3,937,730 and German Offenlegungsschrift No. 2,328,340 of the formula

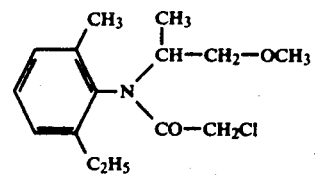

1 Pre-emergence application as tank mixture (a) After sowing

Aqueous stock liquors (suspensions from formulated wettable powders of the herbicide (substance H) and the antidote of formula I (substance S) according to the invention were produced. These were then applied, both separately and as mixtures at the given concentrations and in the given mixture ratios, directly after the sowing of various varieties of cultivated millet, namely Sorghum hybridum (varieties "Funk", "Dekalb", NK "222" and "DC 59"), in pots or in seed trays in a greenhouse, the said liquors being applied to the surface of the soil in the sown vessels. The pots or seed trays were then kept at 22°–23° C. with the required amount of watering, and the results were evaluated after 15 days according to the following ratings:

| | |
|---|---|
| 9 = | plants undamaged (as in the case of the untreated control plants), |
| 1 = | plants completely destroyed, |
| 2–8 = | intermediate stages of damage. |

(b) Before sowing (PPI)

In the same manner as under (a), soil in pots and in seed trays was treated with the liquors containing the active substance, and immediately afterwards these vessels were sown with seed of the millet variety "Funk".

The results are summarised in the following Table I. The concentration values in kg/hectare in relation to the other units of measure are as follows:

1 kg/hectare=0.1 g/m²=2 mg per liter of soil (since seed trays and pots are filled with soil to a depth of 5 cm).

TABLE I

| Applied concentration in kg/hectare | | Variety of Sorghum hybridum | | | | | | | | | | | | | | |
|---|---|---|---|---|---|---|---|---|---|---|---|---|---|---|---|---|
| Substance | | after sowing Funk b | | | before sowing | | | | | | | | | | | |
| | | | | | Funk a | | | Dekalb | | | NK222 | | | DC59 | | |
| H | S | H | H+S | S | H | H+S | S | H | H+S | S | H | H+S | S | H | H+S | S |
| 2.0 | 4.0 | 1 | 9 | 9 | | | | | | | | | | | | |
| 2.0 | 2.0 | 1 | 9 | 9 | | | | | | | | | | | | |
| 4.0 | 16.0 | | | | 1 | 8 | 9 | 1 | 8 | 9 | 1 | 9 | 9 | 2 | 9 | 9 |
| 4.0 | 8.0 | | | | | 6 | | | 6 | | | 6 | | | 6 | |
| 2.0 | 8.0 | | | | 2 | 9 | 9 | 2 | 8 | 9 | 2 | 9 | 9 | 2 | 9 | 9 |
| 2.0 | 4.0 | | | | | 8 | 9 | | 8 | 9 | | 9 | 9 | | 9 | 9 |

It is seen that the cultivated millet varieties remain virtually unaffected with the application of various mixture ratios H:S at the different concentrations, whereas with application of the herbicide H alone they are completely destroyed even at low concentrations.

(2) Seed dressing (wet)

Aqueous emulsion concentrates (liquid) of the antidote according to the invention were prepared, and the cultivated-millet seed (50 g of seed) in a bottle was treated therewith by shaking. The various concentrations of antidote were expressed in grams of antidote per 100 kg of seed. Shortly after this dressing treatment, the seed was sown in pots or in seed trays and then treated in the usual manner (preemergence) as described under 1(a). The results were evaluated 15 days after application of the herbicide using the same ratings as before; the results are listed in the following Table II.

TABLE II

| Applied concentration | | Variety of Sorghum hybridum | | | | | | | | | | | |
|---|---|---|---|---|---|---|---|---|---|---|---|---|---|
| Substance S g/100 kg of seed | Herbicide H kg/hectare | Funk | | | Dekalb | | | NK222 | | | DC59 | | |
| | | H | H+S | S | H | H+S | S | H | H+S | S | H | H+S | S |
| 150 | 4 | 1 | 8 | 8 | 1 | 5 | 9 | 1 | 5 | 8 | 2 | 5 | 8 |
| 75 | 4 | | 9 | 9 | | 7 | 9 | | 8 | 9 | | 8 | 9 |
| 37.5 | 4 | | 9 | 9 | | 3 | 9 | | 6 | 9 | | 7 | 9 |
| 150 | 2 | 2 | 9 | | 2 | 8 | | 2 | 8 | | 2 | 8 | |
| 75 | 2 | | 9 | | | 9 | | | 9 | | | 9 | |
| 37.5 | 2 | | 9 | | | 9 | | | 9 | | | 9 | |

It is seen here too that complete protection of the cultivated millet is obtained where the concentration of herbicide H is low, but sufficiently high to combat weeds, even with low applied amounts of the antidote S. With higher doses of herbicide, the results are somewhat different depending on the variety of cultivated millet used; however, in the case of the "Funk" variety, the results are still optimum.

It was possible also in field tests to confirm these excellent results, whereby it was shown that somewhat better results can be obtained with the seed dressing method than with the tank mixture method.

EXAMPLE III

Tests with Metolachlor

Further tests of the antidote compound of formula I (substance S) applied as a seed treatment were carried out, using metolachlor as the herbicide.

Flat pans, 12.7×17.8 cm in dimension, containing field soil (Leon sand, O.M. 2.8%) were planted to sorghum seed (hybrid G-6-22 GBR) and treated as shown in Table III. The seeds were treated and supplied by Funk Seed Company.

TABLE III

| Lot | Treatment | Treatment Rate | | Amt. of Form./10 kgs Seed | |
|---|---|---|---|---|---|
| | | Std. Treatment[2] | Substance S | Std. Treatment | Substance S |
| 1. | Raw Seed | 0 | 0 | 0 | 0 |
| 2. | Substance S | 0 | ½ | 0 | 20 ml. |
| 3. | Substance S | 0 | 1 | 0 | 40 ml. |
| 4. | Substance S | 0 | 2 | 0 | 80 ml. |
| 5. | Std. Treatment | 1.87 | 0 | 18.8 | 0 |
| 6. | Std. Treatment +Substance S | 1.87 | ½ | 18.8 | 20 ml. |
| 7. | Std. Treatment +Substance S | 1.87 | 1 | 18.8 | 40 ml. |
| 8. | Std. Treatment +Substance S | 1.87 | 2 | 18.8 | 80 ml. |
| 9. | Std. Treatment + Substance S | 1.87 | 1 | 18.8 | 40 ml. |

[1] Grams Substance S/kg of seed
[2] Standard seed treatment-Orthocide 75-3 (Chevron Chemical Co.)-75% captan + 3 % methoxychlor
[3] Standard treatment applied, seed dried then applied.
[4] Applied as a pre-treatment mixture, i.e. standard treatment and Substance S were combined and applied as a single treatment.

Metolachlor was applied broadcast preemergence in the equivalent of 467 liters/Ha of water at 1.12, 1.40, 1.68, 1.96, 2.24, 2.52 and 2.80. Each treatment was replicated four times. All plantings received overhead irrigation within 24 hours following treatment. Average high temperatures for the test period was 28° C. and the average low was 21° C. Phytotoxicity ratings and stand counts were made 7, 14, and 21 days after treatment and sorghum plants were clipped, oven dried (48 hours at 72° C.), and weighed at termination of test (21 days) to determine dry weight/replication.

The results of this test are shown in Table IV.

TABLE IV

| Metolachlor Kg ai/Ha | Seed Lot Number | Sorghym Phytotoxicity[a] | | | Sorghum Stand Count[b] | | | Ave[c] Dry Wt. |
|---|---|---|---|---|---|---|---|---|
| | | 7 Day | 14 Day | 21 Day | 7 Day | 14 Day | 21 Day | |
| 0.00 | 1 | 0.0 | 0.0 | 0.0 | 18.00 | 18.25 | 18.25 | 2.95 |

TABLE IV-continued

| Metolachlor Kg ai/Ha | Seed Lot Number | Sorghym Phytotoxicity[a] 7 Day | 14 Day | 21 Day | Sorghum Stand Count[b] 7 Day | 14 Day | 21 Day | Ave[c] Dry Wt. |
|---|---|---|---|---|---|---|---|---|
| 1.12 | 1 | 8.0 | 7.0 | 7.0 | 20.00 | 19.25 | 11.25 | 0.47 |
| 1.40 | 1 | 9.0 | 8.0 | 9.0 | 19.00 | 15.50 | 3.75 | 0.11 |
| 1.68 | 1 | 9.0 | 8.0 | 9.0 | 16.25 | 15.00 | 5.25 | 0.20 |
| 1.96 | 1 | 9.0 | 8.0 | 9.5 | 17.75 | 17.25 | 2.25 | 0.05 |
| 2.24 | 1 | 9.0 | 8.0 | 9.0 | 19.25 | 18.50 | 2.75 | 0.08 |
| 2.52 | 1 | 9.0 | 8.0 | 9.5 | 18.75 | 12.25 | 0.75 | 0.03 |
| 2.80 | 1 | 9.0 | 9.0 | 9.5 | 19.00 | 16.75 | 1.50 | 0.04 |
| 0.00 | 2 | 0.0 | 0.0 | 0.0 | 18.50 | 18.25 | 18.50 | 3.47 |
| 1.12 | 2 | 7.0 | 5.0 | 3.0 | 18.00 | 18.75 | 15.50 | 1.43 |
| 1.40 | 2 | 7.0 | 5.0 | 3.0 | 18.75 | 17.50 | 14.75 | 1.45 |
| 1.68 | 2 | 7.5 | 4.0 | 3.0 | 17.75 | 18.25 | 15.50 | 1.14 |
| 1.96 | 2 | 7.5 | 6.0 | 4.0 | 19.25 | 16.25 | 13.00 | 1.06 |
| 2.24 | 2 | 8.0 | 7.0 | 6.0 | 19.25 | 16.00 | 8.75 | 0.59 |
| 2.52 | 2 | 8.0 | 7.0 | 6.0 | 18.75 | 15.00 | 8.50 | 0.51 |
| 2.80 | 2 | 8.5 | 7.0 | 7.0 | 18.25 | 16.25 | 10.50 | 0.43 |
| 0.00 | 3 | 0.0 | 0.0 | 0.0 | 17.75 | 18.00 | 17.50 | 2.98 |
| 1.12 | 3 | 3.5 | 4.0 | 2.0 | 17.00 | 17.75 | 17.50 | 1.88 |
| 1.40 | 3 | 3.5 | 3.0 | 1.0 | 18.75 | 19.00 | 17.25 | 2.16 |
| 1.68 | 3 | 4.0 | 3.0 | 1.0 | 18.50 | 18.50 | 18.50 | 1.97 |
| 1.96 | 3 | 4.0 | 4.0 | 2.0 | 17.75 | 17.50 | 16.75 | 1.53 |
| 2.24 | 3 | 7.0 | 5.0 | 3.0 | 17.25 | 16.75 | 14.50 | 1.38 |
| 2.52 | 3 | 7.0 | 6.0 | 3.0 | 18.25 | 18.00 | 16.50 | 1.44 |
| 2.80 | 3 | 8.0 | 6.0 | 4.0 | 18.75 | 18.50 | 14.75 | 0.96 |
| 0.00 | 4 | 0.0 | 0.0 | 0.0 | 19.00 | 19.00 | 19.00 | 2.53 |
| 1.12 | 4 | 2.0 | 0.0 | 0.0 | 17.25 | 17.75 | 17.50 | 2.27 |
| 1.40 | 4 | 0.0 | 0.0 | 0.0 | 18.25 | 18.75 | 18.50 | 2.07 |
| 1.68 | 4 | 3.0 | 2.0 | 0.0 | 17.00 | 17.25 | 17.00 | 2.16 |
| 1.96 | 4 | 3.0 | 3.0 | 0.0 | 15.75 | 16.50 | 16.50 | 2.37 |
| 2.24 | 4 | 5.0 | 4.0 | 2.0 | 16.30 | 17.00 | 16.25 | 1.59 |
| 2.52 | 4 | 4.5 | 4.0 | 1.0 | 16.00 | 16.00 | 15.50 | 1.59 |
| 2.80 | 4 | 5.0 | 5.0 | 0.0 | 15.00 | 16.50 | 15.00 | 1.62 |
| 0.00 | 5 | 0.0 | 0.0 | 0.0 | 18.75 | 19.25 | 19.00 | 3.34 |
| 1.12 | 5 | 7.0 | 7.0 | 6.0 | 18.75 | 16.75 | 10.50 | 0.46 |
| 1.40 | 5 | 8.0 | 8.0 | 8.0 | 18.25 | 15.50 | 3.75 | 0.16 |
| 1.68 | 5 | 8.0 | 8.0 | 8.0 | 18.00 | 16.75 | 4.75 | 0.16 |
| 1.96 | 5 | 8.0 | 8.0 | 8.0 | 18.50 | 15.50 | 3.75 | 0.17 |
| 2.24 | 5 | 9.0 | 8.0 | 9.0 | 17.50 | 16.25 | 6.25 | 0.15 |
| 2.52 | 5 | 9.0 | 9.0 | 9.8 | 18.00 | 10.25 | 0.75 | 0.02 |
| 2.80 | 5 | 9.0 | 8.0 | 8.0 | 17.50 | 16.00 | 4.00 | 0.1 |
| 00.0 | 6 | 0.0 | 0.0 | 0.0 | 17.75 | 18.75 | 17.75 | 2.66 |
| 1.12 | 6 | 3.5 | 3.0 | 4.0 | 18.75 | 18.75 | 17.25 | 1.48 |
| 1.40 | 6 | 4.0 | 4.0 | 2.0 | 16.50 | 16.75 | 16.25 | 1.76 |
| 1.68 | 6 | 4.0 | 5.0 | 2.0 | 18.50 | 18.50 | 18.00 | 1.66 |
| 1.96 | 6 | 5.0 | 5.0 | 2.0 | 18.00 | 17.75 | 16.75 | 1.37 |
| 2.24 | 6 | 6.0 | 5.0 | 5.0 | 18.25 | 18.50 | 17.25 | 0.93 |
| 2.52 | 6 | 6.0 | 6.0 | 4.0 | 18.00 | 15.25 | 11.75 | 0.89 |
| 2.80 | 6 | 6.0 | 5.0 | 4.0 | 19.00 | 18.25 | 13.75 | 0.99 |
| 00.0 | 7 | 0.0 | 0.0 | 0.0 | 18.75 | 19.25 | 19.00 | 2.49 |
| 1.12 | 7 | 3.0 | 3.0 | 3.5 | 19.50 | 18.75 | 18.25 | 1.60 |
| 1.40 | 7 | 3.5 | 3.0 | 1.0 | 17.75 | 18.25 | 17.50 | 2.02 |
| 1.68 | 7 | 3.5 | 4.0 | 2.0 | 19.00 | 18.25 | 17.75 | 1.66 |
| 1.96 | 7 | 3.5 | 3.0 | 1.0 | 19.00 | 19.25 | 17.50 | 2.11 |
| 2.24 | 7 | 4.0 | 4.0 | 2.0 | 18.25 | 18.25 | 17.00 | 1.75 |
| 2.52 | 7 | 4.0 | 4.0 | 2.0 | 19.25 | 19.50 | 18.00 | 1.76 |
| 2.80 | 7 | 4.0 | 4.0 | 3.0 | 19.00 | 19.00 | 16.75 | 1.44 |
| 0.00 | 8 | 0.0 | 0.0 | 0.0 | 17.75 | 18.50 | 17.75 | 2.81 |
| 1.12 | 8 | 1.0 | 0.0 | 0.0 | 18.70 | 19.25 | 18.75 | 2.33 |
| 1.40 | 8 | 1.0 | 0.0 | 0.0 | 17.75 | 18.50 | 17.50 | 2.45 |
| 1.68 | 8 | 1.0 | 2.0 | 0.0 | 18.50 | 18.75 | 19.25 | 2.19 |
| 1.96 | 8 | 2.0 | 2.0 | 1.0 | 17.25 | 18.75 | 17.25 | 2.04 |
| 2.24 | 8 | 2.0 | 2.0 | 1.0 | 18.00 | 18.00 | 18.00 | 1.94 |
| 2.52 | 8 | 3.5 | 4.0 | 1.0 | 18.50 | 18.25 | 16.75 | 1.77 |
| 2.80 | 8 | 4.0 | 3.0 | 3.0 | 17.50 | 18.50 | 17.00 | 1.68 |
| 0.00 | 9 | 0.0 | 0.0 | 0.0 | 18.75 | 18.75 | 18.50 | 2.85 |
| 1.12 | 9 | 3.0 | 1.0 | 0.0 | 18.50 | 18.75 | 18.75 | 2.15 |
| 1.40 | 9 | 3.0 | 3.0 | 0.0 | 18.75 | 18.00 | 17.50 | 2.30 |
| 1.68 | 9 | 3.0 | 3.0 | 5.0 | 19.00 | 18.75 | 18.50 | 1.87 |
| 1.96 | 9 | 4.0 | 5.0 | 3.0 | 18.25 | 17.00 | 14.00 | 1.50 |
| 2.24 | 9 | 4.0 | 5.0 | 4.0 | 18.25 | 17.50 | 14.25 | 1.11 |
| 2.52 | 9 | 6.0 | 6.0 | 5.0 | 18.25 | 16.50 | 12.75 | 1.10 |
| 2.80 | 9 | 7.0 | 6.0 | 6.0 | 16.25 | 14.25 | 10.25 | 0.64 |

[a] Zero equals no effect and ten equals complete control.
[b] Average/replication number of plants emerged (20 seeds planted/replication).
[c] Average dry weight/replication expressed in grams.

The addition of Substance S as a seed treatment at all rates safened (decreased phytotoxicity, and increased seed count) sorghum seedlings against damage by metolachlor at all tested herbicide rates. The greatest degree of safening existed in seed lots 4 and 8 which received 2.0 pgm Substance S kg seed. Seed lot 4 did not receive the standard fungicide and insecticide treatment whereas seed lot 8 did receive this treatment. Table IV shows the phytotoxicity ratings and stand counts for the various seed lots at 7, 14, and 21 days after treatment and the average dry weight at 21 days. One of the most notable ppoints from this table is the lack of reduction in stand count at the 7 and 14 day ratings. Phytotoxicity at these early ratings when so safener was present was high. However, the seedlings were still able to emerge. At the 21 day rating, the stand count in the seed samples with low levels of safener or without safener all had decreased significantly because the affected plants had all died by this later date. With seed lot 5 and 2.80 kg ai/kg metolachlor, dry weight per replication was only 0.18 g whereas the average for seed lot 8, this weight was 1.68. This comparison shows the significant effect the safener has on herbicide activity.

Combinations of metolachlor or other chloroacetanilides with certain triazine herbicides, including ametryn (2-ethylamino-4-isopropylamino-6-methylthio-s-triazine), atrazine (2-chloro-4-ethylamino-6-isopropylamino-s-triazine), prometryn [2,4-bis(isopropylamino)-6-methylthio-s-triazine], propazine [2-chloro-4,6-bis(isopropylamino)-s-triazine], simazine [2-chloro-4,6-bis(ethylamino)-s-triazine], terbuthylazine (2-tert.butylamino-4-chloro-6-ethylamino-s-triazine) and terbutryn (2-tert.butylamino-4-ethylamino-6-methylthio-s-triazine), are excellent for the control of weeds in crop cultures. The use of the antidote of formula I permits those combination herbicides—particularly metolachlor in combination with atrazine, propazine, terbuthylazine and terbutryn—to be used safely in various crops such as sorghum.

EXAMPLE IV

Tests with other chloroacetanilides

The efficacy of the antidote of formula I was tested for its safening effect in conjunction with chloroacetanilides other than metolachlor. The chloroacetanilides tested were:

Substance A—N-(2'-methoxyethyl)-2,6-dimethylchloroacetanilide

Substance B—N-[3'-methoxyprop-(2')-yl]-2,6-dimethylchloroacetanilide

Substance C—N-[2'-methoxyprop-(1')-yl]-2,6-dimethylchloroacetanilide

Substance D—N-[2'-methoxyprop-(1')-yl]-2-methyl-6-ethyl-chloroacetanilide

Substance E—N-[3'-ethoxyprop-(2')-yl]-2-methyl-6-ethyl-chloroacetanilide

Substance F—N-(2'-ethoxyethyl)-2-fluoro-chloroacetanilide

Substance G—N-[3'-ethoxyprop-(2')-yl]-2-fluoro-chloroacetanilide

Substance J—N-[3'-methoxybut-(2')-yl]-2,6-dimethyl-chloroacetanilide

Substance L—N-methoxymethyl-2,6-diethyl-dichloroacetanilide (alachlor)

Sorghum hybridum seed (variety "Funk") and Möhlin-type soil were employed. Tests were run as (1) pre-emergent application of a tank mixture of herbicide and safener and (2) seed dressing. Both types of tests were performed according to the manner of Example II.

For the tank mixture, the dosage rates were, per part of herbicide, 4 parts, 2 parts and 1 part safener. For the seed dressing, the dosage rates were 37.5, 75 and 150 grams of antidote compound (Substance S) per 100 kg of seed.

The results are shown in Table V, where the rating scale used is that of Example II.

TABLE V

| Herbicide Substance | Herbicide kg/Ha | Herbicide alone | Tank Mixture 1:4 | Tank Mixture 1:2 | Tank Mixture 1:1 | Seed Dressing 150 gms | Seed Dressing 75 gms | Seed Dressing 37.5 gms |
|---|---|---|---|---|---|---|---|---|
| A | 2 | 1 | 2 | 2 | — | — | 4 | 2 |
| B | 2 | 1 | 5 | 5 | — | — | 8 | 6 |
| C | 4 | 2 | 2 | 2 | — | 6 | 3 | 2 |
| D | 4 | 2 | 3 | 2 | — | 6 | 5 | 5 |
| E | 4 | 2 | 4 | 4 | — | 7 | 6 | 6 |
| F | 4 | 3 | 6 | 6 | — | 8 | 9 | 9 |
| G | 4 | 2 | 5 | 5 | — | 7 | 6 | 3 |
| J | 4 | 2 | 7 | 4 | — | 9 | 8 | 7 |
| L | 4 | 2 | 7 | 6 | 4 | — | 9 | 8 |

These data show that the antidote compound of formula I is effective as a safener in conjunction with a broad range of chloroacetanilide herbicides.

EXAMPLE V

Tests with other herbicides

The efficacy of the antidote of formula I was tested for its safening effect in conjunction with herbicides other than chloroacetanilides. The herbicides tested were:

Substance M—S-ethyl-N,N-diisobutylthiocarbamate (butylate)

Substance N—2-chloro-N-isopropylacetanilide (propachlor)

Test methods were the same as in Example IV.

The results are shown in Table VI.

TABLE VI

| Herbicide Substance | Herbicide kg/Ha | Herbicide alone | Tank Mixture 1:4 | Tank Mixture 1:2 | Tank Mixture 1:1 | Seed Dressing 75 gms | Seed Dressing 37.5 gms |
|---|---|---|---|---|---|---|---|
| M | 4 | 3 | 4 | 4 | 5 | 8 | 7 |
| N | 16 | 6 | 7 | 7 | 8 | 9 | 9 |

The antagonistic action of the antidote according to the invention does not extend to the principal weeds normally associated with cultivated plants, e.g. Echinochloa, Setaria italica, Digitaria sanguinalis, etc. These weeds are destroyed by the herbicides used with the antidote practically to the same high degree as that resulting without the presence of the antidote.

Also insecticides, fungicides, etc., such as Diazinon, captan, methoxychlor and so forth, do not lose their effectiveness as a result of the antidote; such insecticides can therefore be concomitantly used in seed dressing.

EXAMPLE VI

Safening in rice crops

Good "safening" effects similar to those resulting with the use of the herbicide H can be obtained when the oxime ether according to the invention is employed with thiolcarbamates and with other chloroacetanilides even on other crops, as is shown by the following test with rice where N-[2'-n-propoxyethyl]-2,6-diethylchloroacetanilide of the formula

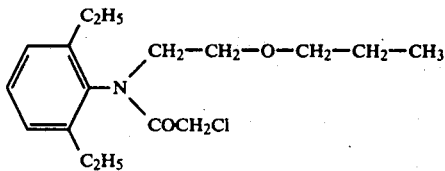

is used as the herbicide (K).

Rice is grown in very moist soil until the plants are carrying 3 to 4 leaves. The plants are then taken from the soil and the adhering soil is washed from the roots with water. The roots are thereupon immersed for 30 minutes in aqueous preparations containing respectively 125, 32, 8 and 2 ppm (=parts of active substance per $10^6$ parts of the "solution") of the antidote, phenyl-glyoxylonitrile-2-oxime-cyanomethyl ether.

The rice plants treated in this manner are then planted in soil in containers having a surface area of 12 cm × 8 cm and a depth of 15 cm (96 cm² surface area and 1.44 liters volume per container). The height of water is subsequently adjusted to 2 cm. Spraying is carried out after 10 days with a 0.4% liquor of the herbicide K [N-(2'-n-propyloxyetyl)-2,6-diethyl-N-chloroacetanilide], the equivalent amount of liquor being 500 liters per hectare or 2 kg/hectare (=0.5 cm³ of liquor per container). The liquor is sprayed over the leaves of the rice plants and into the water. The test is evaluated 20 days after the treatment with the herbicide. Evaluation is on the basis of the scale of ratings used in the test with millet (9=normal condition; 1=completely destroyed).

The results are summarised in the following table:

TABLE VII

| | | Toxicities on rice | | |
|---|---|---|---|---|
| Conc. herbicide K | Conc. antidote S | K (alone) | K + S | S (alone) |
| 2 kg/ha | 125 ppm | 4 | 8 | 9 |
| 2 kg/ha | 32 ppm | 4 | 7 | 9 |
| 2 kg/ha | 8 ppm | 4 | 8 | 9 |
| 2 kg/ha | 2 ppm | 4 | 8 | 9 |

What is claimed is:

1. A method for protecting crops from injury caused by application of a herbicidal thiocarbamate of the formula

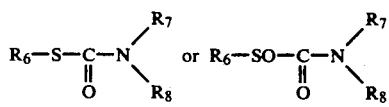

wherein
$R_6$ is lower alkyl, lower alkenyl, chloroallyl, dichloroallyl, trichloroallyl or p-chlorobenzyl,
$R_7$ is lower alkyl having at least 2 carbon atoms, and
$R_8$ is lower alkyl having at least 2 carbon atoms or cyclohexyl or wherein
$R_7$ and $R_8$ together with the nitrogen atom form the hexahydro-1H-azepin ring or the decahydroquinoline or 2-methyl-decahydroquinoline ring,
said method comprising applying to the crop seeds, a crop protecting amount of phenylglyoxylonitrile-2-oxime-cyanomethyl ether.

2. A method for selectively controlling weeds in sorghum cultures which comprises applying to a culture of sorghum grown from seeds treated with a safening amount of phenylglyoxylonitrile-2-oxime-cyanomethyl ether, a herbicidally effective amount of a thiocarbamate compound of the formula

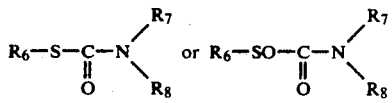

wherein
$R_6$ is lower alkyl, lower akenyl, chloroallyl, dichloroallyl, trichloroallyl or p-chlorobenzyl,
$R_7$ is lower alkyl having at least 2 carbon atoms, and
$R_8$ is lower alkyl having at least 2 carbon atoms or cyclohexyl or wherein
$R_7$ and $R_8$ together with the nitrogen atom form the hexahydro-1H-azepin ring or the decahydroquinoline or 2-methyl-decahydroquinoline ring.

3. The method according to claim 2 in which the thiocarbamate compound is S-ethyl-N,N-diisobutylthiocarbamate.

4. Rice or sorghum seed, the plants grown from which are resistant to injury by pre-emergence application of a herbicidal compound of the formula

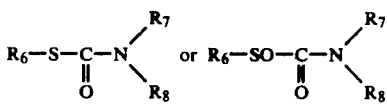

wherein
$R_6$ is lower alkyl, lower alkenyl, chloroallyl, dichloroallyl, trichloroallyl or p-chlorobenzyl,
$R_7$ is lower alkyl having at least 2 carbon atoms, and
$R_8$ is lower alkyl having at least 2 carbon atoms or cyclohexyl or wherein
$R_7$ and $R_8$ together with nitrogen atom form the hexahdro-1H-azepin ring or the decahydroquinoline or 2-methyl-decahydroquinoline ring,
said seed being coated with phenylglyoxylonitrile-2-oxime-cyanomethyl ether in an amount ranging from about 5 to about 500 grams per 100 kilograms of seed.

5. Seed according to claim 4 in which the herbicidal compound is S-ethyl-N,N-diisobutylthiocarbamate.

6. Seed according to claim 4 which is coated with phenylglyoxylonitrile-2-oxime-cyanomethyl ether in an amount ranging from about 50 to 400 grams per 100 kilograms of seed.

7. A method for protecting a sorghum crop from injury caused by application of the herbicide S-ethyl-N,N-diisobutylthiocarbamate, which method comprises applying to the soil in the rows of seed, prior to treatment with said herbicide, a crop-protecting amount of phenylglyoxylonitrile-2-oxime-cyanomethyl ether.

8. A method for protecting crops from injury caused by the application of S-ethyl-N,N-diisobutylthiocarbamate which comprises treating crop seeds with a crop-protecting amount of phenylglyoxylonitrile-2-oxime-cyanomethyl ether.

9. A method according to claim 8 in which the crop is sorghum.

* * * * *